United States Patent [19]

Jett-Tilton et al.

[11] Patent Number: 4,999,344

[45] Date of Patent: Mar. 12, 1991

[54] PHOSPHATIDYL TREATMENT OF RAPIDLY PROLIFERATING CELLS

[75] Inventors: Marti Jett-Tilton, Washington, D.C.; Carl R. Alving, Bethesda, Md.

[73] Assignee: The United States of America as represented by the Secretary of the Army, Washington, D.C.

[21] Appl. No.: 168,079

[22] Filed: Mar. 14, 1988

Related U.S. Application Data

[60] Continuation-in-part of Ser. No. 117,601, Nov. 6, 1987, abandoned, which is a division of Ser. No. 911,689, Sep. 25, 1986, abandoned.

[51] Int. Cl.$^5$ .................. A01N 31/66; A61K 31/685
[52] U.S. Cl. ........................................ 514/77; 514/76; 514/78; 552/506; 552/544
[58] Field of Search ............................ 514/77, 76, 78; 260/397.2

[56] References Cited

PUBLICATIONS

Jett et al., "Metabolic Fate of Liposomal Phosphatidylinositol in Murne Tumor Cells! Implications for the Mechanism of Tumor Cell Cytotoxicity", *Cancer Research* 45, 4810–4815, Oct. 1985.

Jett et al., "Selective Cytotoxicity of Tumor Cells Induced by Liposome Containing Plant Phosphatidylinositol", *Biochem Biophys. Res. Comm.*, vol. 114, No. 2, 1983/Jul., pp. 863–871.

*Primary Examiner*—Nathan M. Nutter
*Attorney, Agent, or Firm*—Werten F. W. Bellamy; Anthony T. Lane

[57] ABSTRACT

Diacyl phosphatides having a polyunsaturated carboxylic acid at the 2 position are found to have cytotoxic effect against tumor cells. Subject compositions may be employed in vivo or in vitro for inhibiting tumor cell growth, either by themselves or in combination with other cytotoxic drugs. The compositions may be administered as liposomes.

48 Claims, 11 Drawing Sheets mole % of ([$^{14}$C] linoleoyl) PI IN PIG LIVER PI mole % of ([$^{14}$C] linoleoyl) PI IN PIG LIVER PI

PHOSPHATIDYL TREATMENT OF RAPIDLY PROLIFERATING CELLS

CROSS-REFERENCE TO RELATED APPLICATIONS

This application is a Continuation-in-part of application Ser. No. 07/117,601 filed Nov. 6, 1987 and now abandoned which in turn is a divisional of application Ser. No. 911,689, filed Sept. 25, 1986, now abandoned whose disclosure is incorporated herein by reference.

INTRODUCTION

1. Technical Field

The field of this invention concerns the treatment of rapidly proliferating cells, particularly neoplastic cells, to diminish the rate of proliferation. The methods employ drugs which act a mitotic inhibitors.

2. Background

Despite the long history of efforts to treat diseases involving rapidly proliferating cells, such as neoplasia and psoriasis, neoplasia remains a debilitating disease afflicting humans and animals alike. While the processes initiating tumors are slowly being unraveled, there is still substantial mystery about how a tumor is initiated, how it manages to elude the defensive mechanisms of the host, the particular metabolic processes involved with the initiation and maintenance of tumors, as well as the metastasis of the tumors. For the most part, approaches have been to inhibit proliferation by inhibiting steps involving DNA replication or other processes involved with mitosis. These approaches have not been restricted to neoplastic cells, but affect all cells undergoing proliferation.

While for the most part, most cells in a mammalian host either are not being duplicated or are undergoing very slow growth, this is not true of the hematopoietic system. Since the hematopoietic system is involved with the immune response, events which adversely affect the multiplication of blood cells have substantial adverse effects on the host. The host's ability to fight the tumor is diminished. At the same time, the host becomes subject to opportunistic infections.

Various efforts have been made to restrict the cytotoxic effects to the tumor. For the most part, these have involved the use of monoclonal antibodies which are directed to a surface membrane protein, which has a much higher incidence on a tumor surface than on normal cell surfaces. However, even this approach has substantial limitations, since even where the incidence of the surface membrane protein is relatively low on normal cells, the much greater number of normal cells as compared to tumor cells adversely affects the health binding of the antibodies. In addition, in many instances, the tumor cells are able to undergo mutations resulting in their ability to evade the effect of the anti-tumor agent.

While substantial strides have been made in improving the treatment of tumor patients, nevertheless there remains ample opportunity for further improvements. The need to provide for agents which have substantial selectivity between normal and abnormal cells is still a major goal. In addition, agents should desirably affect processes peculiar to the tumor cells as distinct from normal cells or at least provide for significant discrimination.

RELEVANT LITERATURE

Jett et al., *Biochem. Biophys. Res. Comm.* (1983) 114:863–871, reported that liposomes containing phosphatidyl inositol (PI), cholesterol, and cholesteryl oleate selectively killed tumor cells from cultured cell lines without harming the normal cells present. Jett et al.. *Cancer Research* (1985) 45:4810–4815, reported that cholesteryl oleate reduced the anti-tumor effect. See also, Jett and Maeyama, *J. Cell Biol.* (1986.) 103:(5)455–455a.

SUMMARY OF THE INVENTION

Proliferation of rapidly dividing cells is inhibited by contacting the cells with a proliferationinhibiting amount of diacyl phosphatide containing a polyunsaturated fatty acid at the 2-carbon position. The phosphatides are found to substantially reduce the formation of tumor cells while having substantially reduced effects on wild-type cells. The phosphatides may be employed as liposomes, by themselves or in conjuction with other lipids or other physiologically active agents.

Figure 5A:
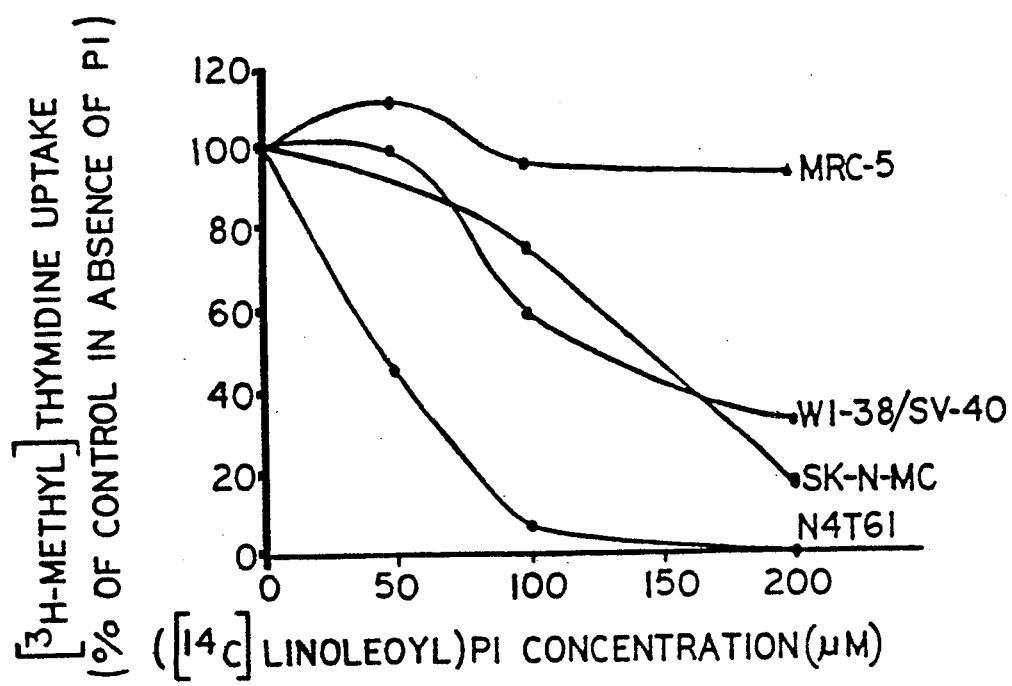
FIGS. 5 through 7 a show comparisons of the effects of liposomes having varous phospholipids containing defined fatty acids on [$^3$H-methyl]-thymidine uptake. Thymidine uptake is a method of assessing cell viability of cultured cells, and decreased thymidine uptake occurs as a result of cytotoxicity caused by contact with toxic substances. △-△, MRC-5 normal embryonic lung fibroblasts; ▲-▲, W1-38SV/40 transformed embryonic human lung fibroblasts; ☐☐, SK-N-MC human glioblastoma cells and ■-■, N4TG1 mouse neuroblastoma cells.
Figure 6A:
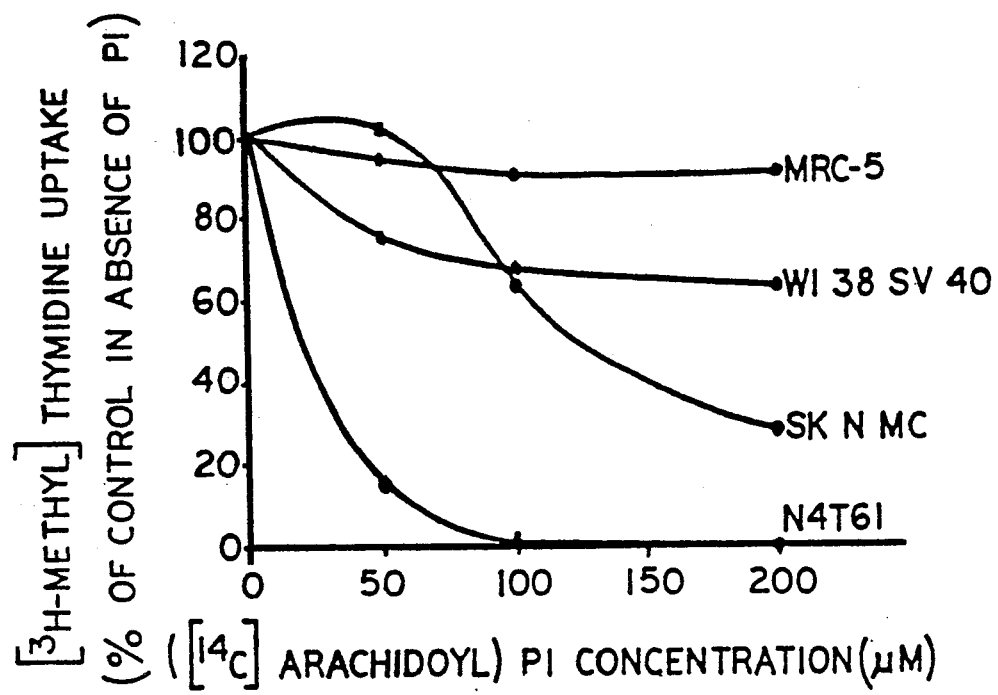
Figure 6B:
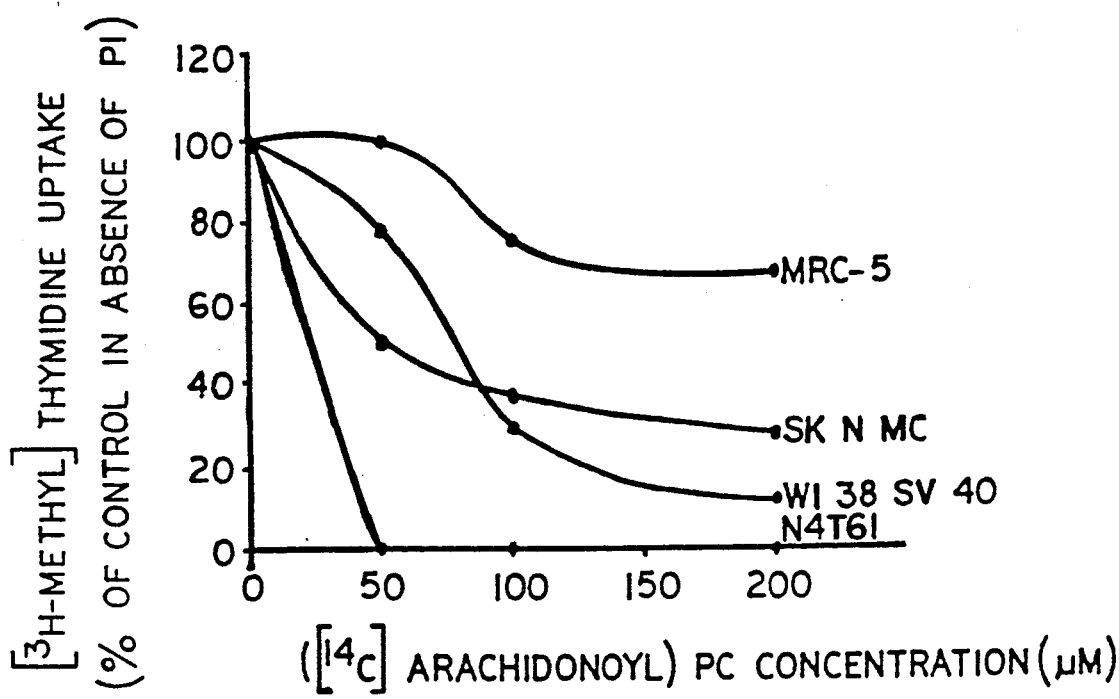
Figure 7A:
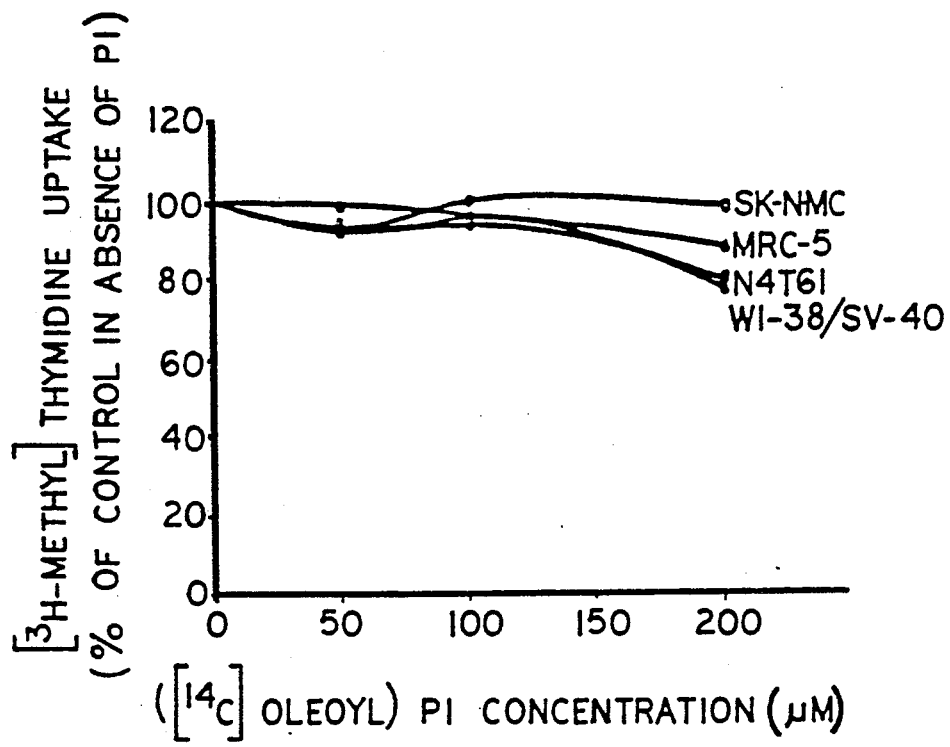
Figure 7B:
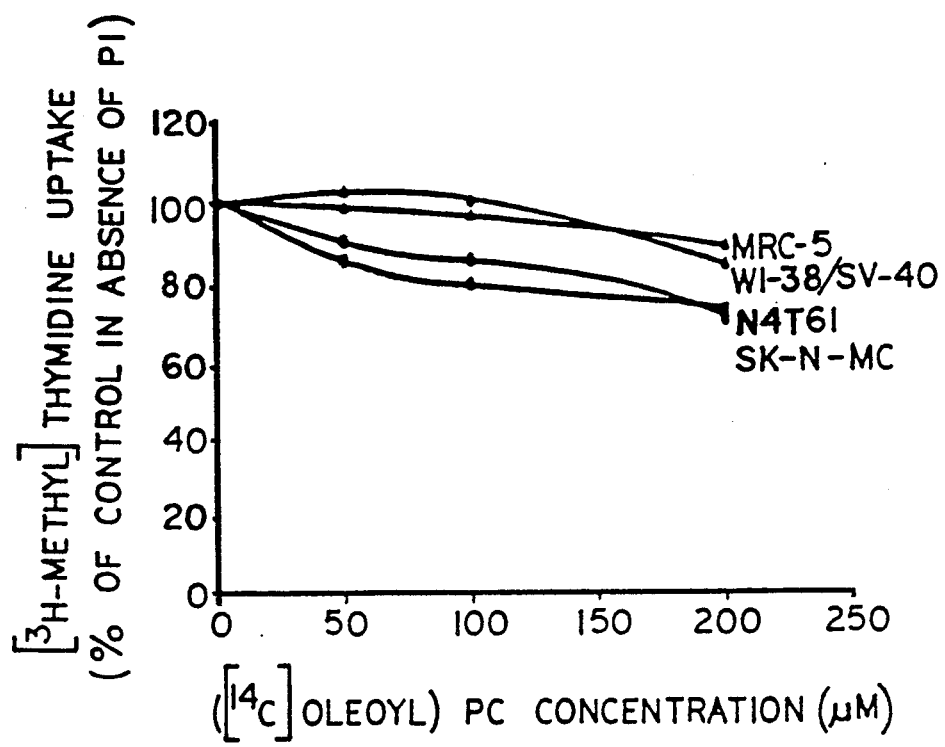

Cells were treated with liposomes containing synthetic preparations of PI (left frames) or PC (right frames) containing palmitic acid in the sn-1 position and either [$^{14}$C]linoleic acid in the sn-2 position (FIGS. 5 and 5a) or [$^{14}$C]arachidonic acid in the sn-2 position (FIGS. 6 and 6a) or [$^{14}$C]oleic acid in the sn-2 position (FIGS. 7 and 7a). The liposomes were comprised of the indicated phospholipids (PI or PC) and cholesterol in a molar ratio of 2:1.

Figure 5B:
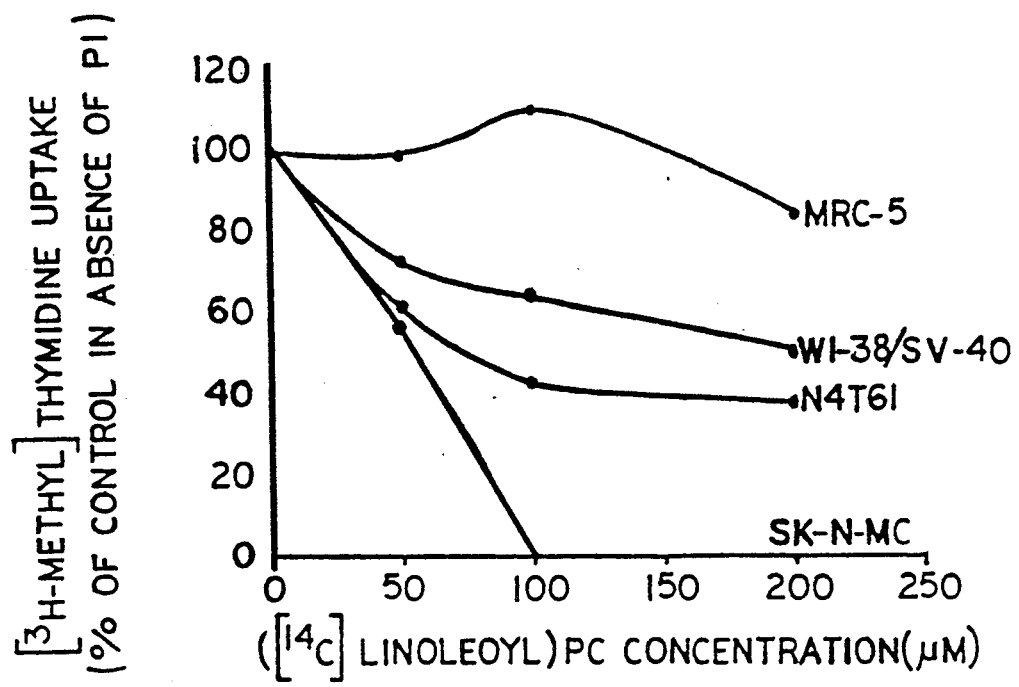

FIGS. 5 through 6a show that glioblastoma (SK-N-MC), neuroblastoma (N4TG1), and virally-infected (WI-38/SV-40) cells are easily killed with phospholipids containing linoleic or arachidonic acid in the sn-2 position whereas FIGS. 7 and 7a show that oleic acid in the sn-2 position has little effect on tumor or normal (MRC-5) cells.

Figure 8:
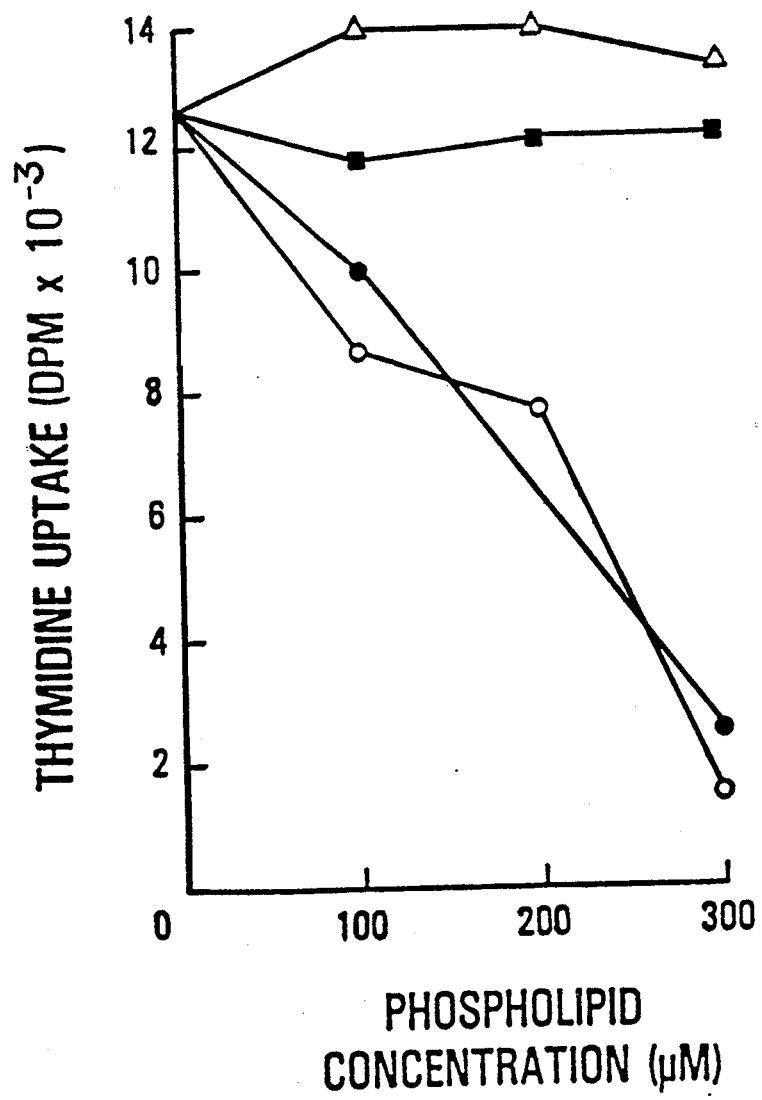

FIG. 8 shows the comparison of the effects of lyso-PI (lacking any sn-2 fatty acid) with other PI preparations on thymidine uptake by N4TG1 neuroblastoma cells ●⊙-lyso-PI, △-Plant PI, △-year PI, and ■-animal PI.

Figure 9A:
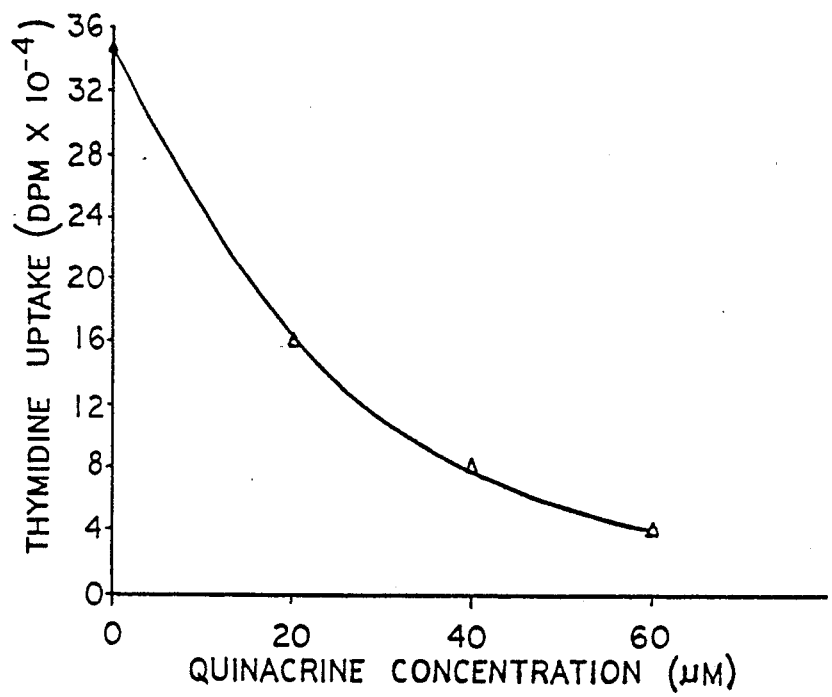
Figure 9B:
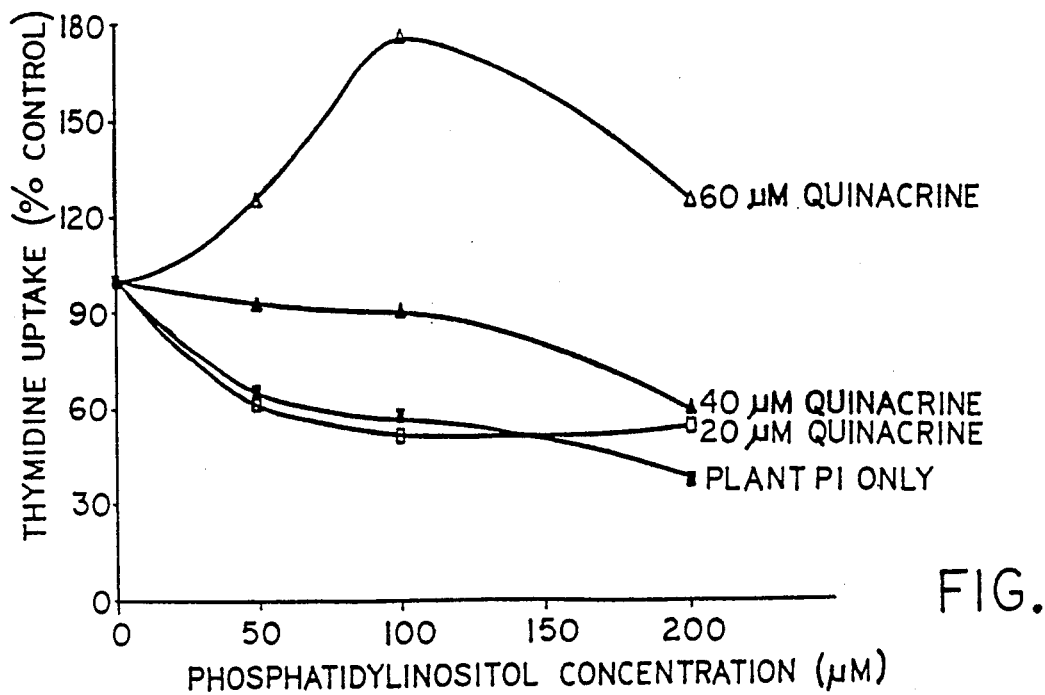

FIGS. 9a, b, c, and d show the effect of inhibitors on PI toxicity to tumor cells. In FIG. 9a, the effect of quinacrine alone on thymidine incorporation by N4TG1 mouse neuroblastoma cells is illustrated, and FIG. 9b shows the effects of different concentrations of quinacrine on cellular toxicity induced by liposomes containing plant PI/cholesterol/([$^{14}$C]linoleoyl)PI (molar ratios of 2/1/0.01).

Figure 9C:
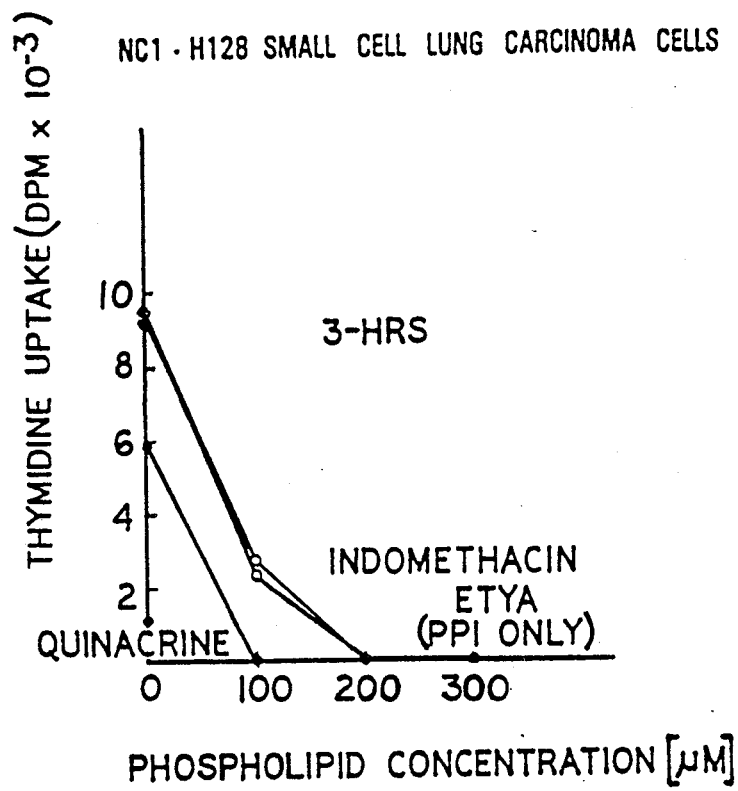
Figure 9D:
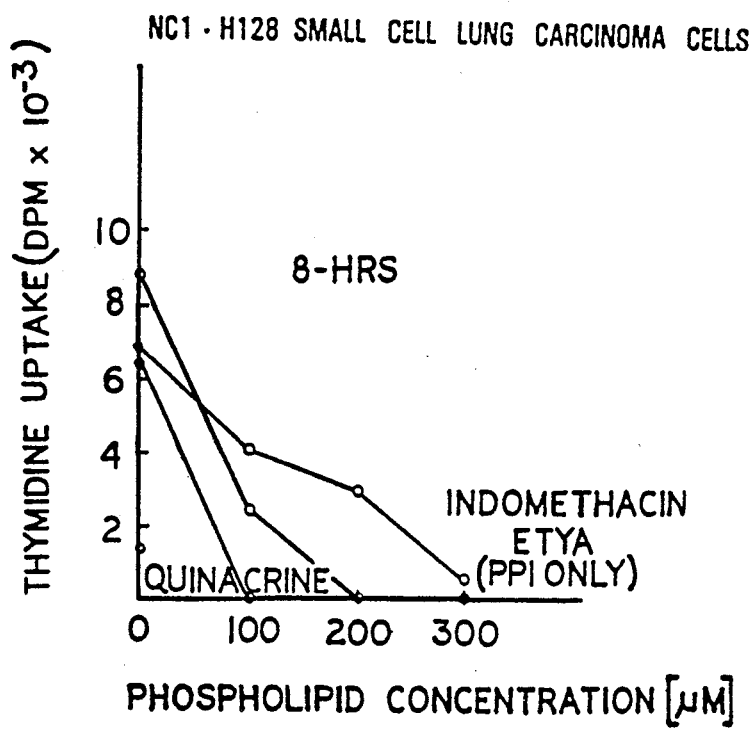
Figure 10:
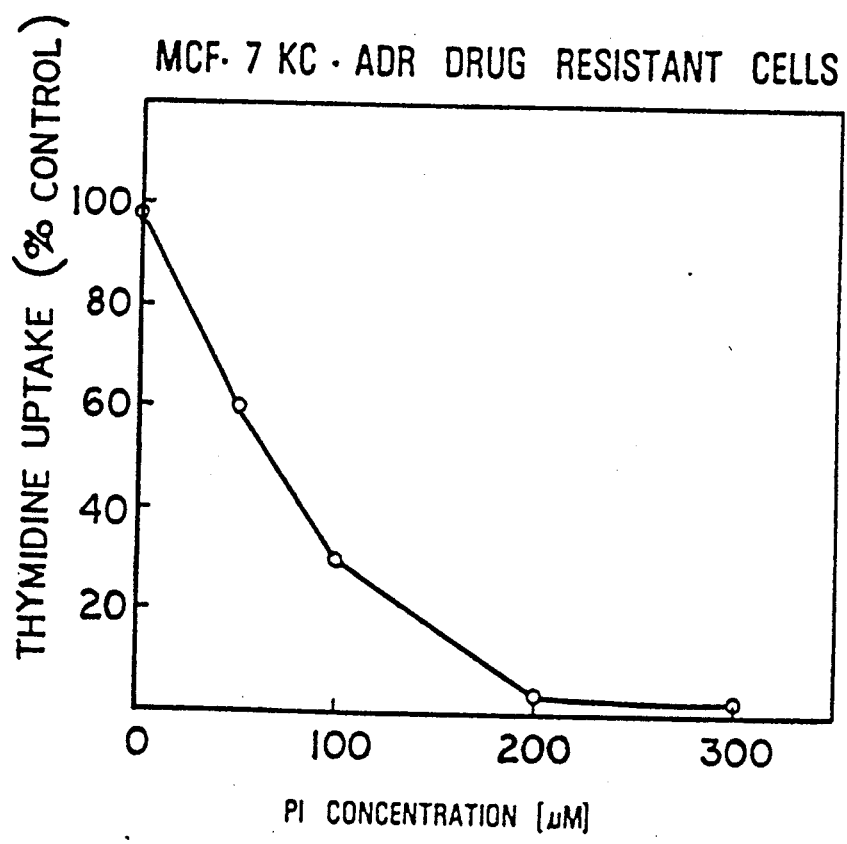

FIGS. 9c and 9d show the effects of inhibitors of phospholipase $A_2$ (quinacrine) or prostaglandin synthesis (eicosanotetraynoic acid) or leukotriene synthesis (indomethacin) on cytotoxicity induced by liposomes containing plant PI/cholesterol/([$^{14}$C]linoleoyl)PI (2/1/0.01). The NCI-H128 cells are a small cell lung carcinoma cultured cell line FIG. 10 shows the toxicity induced by plant PI, to MCF-7 KC-ADR, which are pleiotropic drug resistant cells.

DESCRIPTION OF THE SPECIFIC EMBODIMENTS

Abnormal cells, particularly those having an elevated amount of phospholipase $A_2$, may be inhibited from growing by contact with a growth inhibiting amount of a diacyl phosphatide characterized by having a polyunsaturated fatty acid at the sn-2 position. The phosphatide is further characterized by having at least 17 carbon atoms and usually fewer than 65 carbon atoms, more usually fewer than about 55 carbon atoms, where the sn-1 and sn-2 positions are substituted with carboxylic acids, the sn-2 position having a carboxylic acid having at least 2 aliphatic sites of unsaturation, usually olefinic sites. The phosphatides may be used in the form of liposomes, where the liposome may have the phosphatide as the sole lipid or in combination with other lipids, other than saturated or monounsaturated fatty acids of at least 12 carbon atoms, so as not to significantly interfere with the activity of the phosphatide. In addition, the liposomes may comprise other drugs which may enhance the effectiveness of the subject phosphatides or provide for additional effects.

For the most part, the phosphatides will be phospholipase $A_2$ (PLA$_2$) substrates and have the following formula:

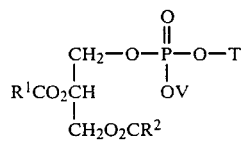

wherein:
T is hydrogen, a physiologically acceptable counterion, e.g. salt, such as sodium, potassium, calcium, etc., inositol, any of its phosphate derivatives, mono-, di- or tri-, including cyclic phosphate; choline, serine, ethanolamine, glycerol, or other group which does not interfere with phospholipase $A_2$ activity;

V is hydrogen or a physiologically acceptable counterion;

$R_1$ is a polyunsaturated aliphatic fatty acid of at least about 10 carbon atoms, preferably at least about 12 carbon atoms, usually not more than about 36 carbon atoms, more usually not more than about 28 carbon atoms, having at least 2 sites of aliphatic unsaturation and may have 6 or more, usually not more than 5, more usually not more than 4, generally from 2 to 4 sites of aliphatic unsaturation;

$R^2$ is a fatty acid of at least 2 carbon atoms and not more than about 36 carbon atoms, generally ranging from about 2, usually 12 to 24 carbon atoms, and may be saturated or unsaturated, having from 0 to 5, usually 0 to 4, more usually 0 to 3 sites, generally 0 to 1, site of aliphatic unsaturation.

The aliphatic unsaturation may be at any site in the fatty acid and may be ethylenic or acetylenic, conjugated or unconjugated, preferably conjugated, where the fatty acid may be naturally occurring or synthetic. There may be from 0 to 2, usually 0 to 1 substituents, particularly oxy, e.g. hydroxyl. The chains may be branched or straight chain, usually straight. For the unsaturated acids, unsaturated acids include linoleic, α- or γ-linolenio, arachidonic, geranic, 9,11-octadecatrienoic acid, dehydrogeranic acid, elaeostearic acid, 6,9,12-octadecatrienoic, stearidonic, clupanadonic, etc. For the saturated or mono-unsaturated fatty acids, the acids include acetic, propionic, butyric, lauric, myristic, palmitic, palmitoleic, oleic, stearic, etc.

The subject compositions may be a single compound or a mixture of compounds, as to the lipids at the 1 and 2 positions (phosphate being the 3 position), or as to the substituent bound to phosphate. Conveniently, naturally occurring compositions may be employed such as plant compositions, from soybean, rape seed, safflower, corn, sunflower, etc., as the inositols, glycerols, cholines, etc., and combinations thereof. The naturally occurring compositions may be extracted, purified, fractionated, or subjected to other treatment.

Specific compounds of interest include sn-3-phosphatidyl-1-palmitoyl-2-linolenoyl inositol; sn-3-phosphatidyl-1-acetyl-2-arachidonyl choline; sn-3-phosphatidyl-1-butyryl-2-eicosatetraenoyl inositol-4-phosphate; sn-3-phosphatidyl-1-lauryl-2-linoleoyl ethanolamine. The subject compounds may be obtained from any source, including plant glycerides, fish glycerides, may be prepared synthetically, or combinations thereof.

The subject compositions may be used by themselves or in conjunction with other fatty acids, particularly when prepared as vesicles or liposomes. Where prepared as liposomes, the subject compositions will be at least about 5 mole percent, more usually at least about 25 mole percent and preferably in the range of about 50 to 80 mole percent, more preferably in the range of about 55 to 75 mole percent. Desirably, the subject compositions should be free of phosphatides which have a saturated or mono-olefinic carboxylic acid at the sn-2 position, as well as lipids, e.g. carboxylates, glycerides, alkyl esters, etc. having fewer than 2 sites of aliphatic unsaturation. The liposomes may be made in accordance with conventional ways, by combining the various lipids, evaporating solvent and the dried lipids suspended in an aqueous medium, and subjecting the medium to rapid agitation, for example, by ultrasonic sound. Other lipids which may be used include cholesterol, polyunsaturated fatty acid esters, e.g. methyl, etc. The resulting vesicles may then be isolated and used. See, for example, Kim and Martin, *Biochem. et Biophys. Acta* (1981) 646:1–9 and U.S. Pat. Nos. 4,311,712; 4,310,506; 4,302,459; 4,261,975; 4,241,046; 4,235,871; 4,229,360; 4,224,179; 4,053,385; 4,016,290 and 3,957,971.

If desired, the liposomes may be modified to direct the liposomes to particular types of cells. Thus, antibodies or ligands for particular receptors may be employed, where the target cell is associated with a particular surface protein. For example, where a higher incidence of a surface membrane protein is found on tumor cells, e.g. growth factor receptors, phospholipase $A_2$, etc. an antibody to such protein may be bound to the liposome surface in accordance with conventional ways. The antibody or other specific binding ligand serves as a site-directing molecule.

The particular ligand or antibody may be conjugated to the liposome in accordance with conventional ways, either by conjugating the site-directing molecule to a lipid for incorporation into the lipid bilayer or by providing for a linking group on a lipid present in the bilayer for linking to a functionality of the site-directing compound.

Relatively small liposomes are preferred. Desirably, the liposomes employed should not sediment at 1000 xg, preferably not sediment at about 1500 xg, and more preferably not sediment at 2000 xg or greater.

The subject compositions may be formulated in a wide variety of ways, employing physiologically acceptable media, such as deionized water, phosphate buffered saline, Ringer's solution, or other appropriate solution. The amount of the active phosphatide may vary widely in the medium, generally ranging from about 100 mg/ml to 1 mg/ml. Depending upon the manner of administration, the frequency, the nature of the target, and the like, usually from about 0.5 g to 800 g of the phosphatide will be used per kg of host, inversely related to the weight of the host. Other compositions may be present, such as stabilizers, buffers to provide a physiological pH, e.g. 6–8.5, or the like.

The subject compositions may be used in the treatment of a wide variety of tumors, both solid and non-solid tumors, including carcinomas, sarcomas, lymphomas, leukemias, etc. The subject compositions may be used in vitro to inhibit tumor cells from growing in culture, particularly where studying normal cells or non-tumorigenic cells. Thus, in studying mechanisms involving tumor formation, immortalization or cellular processes, it may desirable to inhibit the growth of any tumor cells which may form in the system.

The subject compositions have been found to be effective with a wide variety of tumor cells comprising a mammary carcinoma, such MCF-7; bladder carcinoma such as 5637 (bladder, primary carcinoma, Human)-ATCC No. HTB 9; lymphoid cells, such as promeylocytic leukemia cells (HL-60)-ATCC No. CCL 240, and Raji (Burkitt lymphoma)-ATCC No. CCL 86; a neuroblastoma, such as human NB(SK-N-MC)-ATCC No. HTB-10; a glioblastoma, such as U-87 MG (glioblastoma-astrocytoma)-ATCC No. HTB 14; a small cell lung carcinoma, such as NCI-H69 (small cell carcinoma of lung, Human, male)-ATCC No. HTB 119 and NCI-H128 (small cell carcinoma of lung, human)-ATCC No. HTB 120; a lung carcinoma, human, such as SK-MES-1, (lung, carcinoma, human)-ATCC No. HTB-58; melanoma, such as, HT-144 (melanoma, human)-ATCC No. HTB-63; and ascites, such as, Strain E (Ehrlich-Lettre Ascites carcinoma, mouse)-ATCC No. CCL 77, and an ovarian carcinoma, such as, OVCAR 3 (human ovarian carcinoma); and mammary carcinoma, such as MCF-7-KC or MCF-7-KC-ADR drug resistant cells.

The subject method is particularly effective with cells which exhibit multiple drug resistance. This supports a basis for cytotoxicity for tumor cells of the polyunsaturated phosphatides. The polyunsaturated phosphatides appear to be good substrates for $PLA_2$ and poor substrates for phospholipase (PLC). The products of the $PLA_2$ catalyzed reaction lipophosphatides and polyunsaturated fatty acids appear to be competitive inhibitors of PCL, inhibiting the transduction of signals through PLC and inhibiting secondary messenger formation by phospholipase C. Thus, the subject compositions are particularly useful with tumors having the mdr phenotype and may find particular application in conjunction with chemotherapy where tumor cells having the mdr phenotype are involved.

As to diseases which may be treated by the subject compositions, they include leukemias, AML, ALL, CML, etc., lymphomas, lung small cell carcinoma, neuroblastoma, mammary carcinoma, glioblastoma, Hodgkins' disease, hepatoma, melanoma, astrocytoma, colorectal carcinoma, etc.

The subject compositions may be used by themselves or in conjunction with other drugs for the treatment of tumors. Thus, the subject compositions may be prepared with a variety of drugs in the liposome lumen which may serve to enhance the cytotoxic effects of the subject compositions. Other compounds which may find use include mathotrexate, vinblastine, adriamycin, venca alkaloids, 5-fluorouracil, growth factors, antimetabolic agents, cytokines, etc. Administration of these drugs will be in accordance with their usual concentrations or lower dosage levels, as they may provide for greater effectiveness in conjunction with the subject compositions. In this manner, the cytotoxic effect against normal cells can be reduced, by using lower concentrations of the cytotoxic drugs in conjunction with the subject phosphatides.

The subject compounds may be administered systemically by injection into the vascular system, parenterally, by inhalation, orally, intralesionally, or the like. The particular manner of administration may vary with the site of the tumor, whether localized or metastisized, whether solid or non-solid, dosage level, etc.

The following examples are offered by way of illustration and not by way of limitation.

EXPERIMENTAL

The abbreviations used are defined as follows: PI, phosphatidylinositol; DG, diglycerides; ([$^{14}$C]linoleoyl)PI, sn-3-phosphatidyl(1-palmitoyl-2-[1'-$^{14}$C]linoleoyl)myo-inositol; ([$^{14}$C]oleoyl)PI, sn-3-phosphatidyl(1-stearoyl-2-([1'-$^{14}$C]oleoyl)myo-inositol; ([$^{14}$C]arachidonoyl)PI, sn-3-phosphatidyl(1-stearoyl-2-([1'-$^{14}$C]arachidonoyl)myo-inositol; ([$^{3}$H]myoinositol)PI, sn-3-phosphatidyl-([2'-$^{3}$H]myo-inositol; PIP, sn-3-phosphatidylinositol-4-phosphate: $PIP_2$, sn-3-phosphatidylinositol-4,5-dipbosphate.

MATERIALS AND METHODS

Lipids

Soybean PI (containing fatty acids consisting of palmitic, 38.7%, linoleic, 48.9%: oleic, 4.8%: and stearic, 7.6%) and bovine liver PI (containing fatty acids consisting of stearic, 47.3%: arachidonic, 19.6%: linolenic, 12.3%: oleic, 7.1%: linoleic, 5.1%: and palmitic, 4.8.%) were obtained from Avanti Polar Lipids, Inc., Birmingham, AL. Yeast PI was obtained from Serdary Research Laboratories, London, Ontario, Canada, as was porcine liver PI (containing fatty acids consisting of palmitic, 6.2%: stearic, 77.6%: oleic, 9.3%; and linoleic, 6.9%), [12, 13-$^3$H]linoleic acid was obtained from E. I Dupont de Nemours and Company, New England Nuclear (Boston, MA). Nonradioactive linoleic acid and lyso-PI were obtained from Sigma Chemical Company (St. Louis, MO). The following radioactive PI compounds, all supplied by Amersham Corporation, Chicago Heights, IL, were used: sn-3-phosphatidyl(1-palmitoyl-2[1'-$^{14}$C]linoleoyl)myo-inositol (58 mCi/mmol); sn-3-phosphatidyl(1-stearoyl-2[1'-$^{14}$C]oleoyl)myo-inositol (54 mCi/mmol); sn-3-phosphatidyl(1-stearoyl-2[1'-$^{14}$C]arachidonoyl)myoinositol (7 mCi/mmol): sn-3-phosphatidyl [2'-$^3$H]myoinositol (15.5 Ci/mmol). In the penultimate compound, the fatty acid composition was identical to that of ox brain PI so that over 90% of the sn-1 and sn2 positions were occupied by stearoyl and arachidonoyl groups, respectively. All phospholipid preparations were checked for purity and were free of contaminants as determined by thin layer chromatography. Cholesterol (Sigma) was recrystallized 3 times before use. All lipids were stored under nitrogen to avoid lipid peroxidation.

Preparation of Liposomes (Multilamellar Vesicles)

Lipids were dried and resuspended exactly as described previously in the *Biochem. Biophys. Res. Commun.* article. In the use of ([$^{14}$C]linoleoyl)PI, ([$^{14}$C]oleoyl)PI, or ([$^{14}$C]arachidonoyl)PI the phospholipids were used in a 2:1 molar combination with cholesterol. Cholesterol was included in the liposomes in order to minimize the net transfer of cholesterol into or out of the cells. ([$^3$H]myo-Inositol)PI was used as a tracer (1%) with bovine liver PI as the bulk phospholipid carrier for forming liposomes. [$^3$H]Linoleic acid was used as a tracer (4%) in liposomes containing linoleic acid:PI (yeast or animal): cholesterol, 2:1. It was shown that it is not necessary to have cholesterol present to observe the cytotoxicity.

Cell Cultures

The N4TG1 mouse neuroblastoma cell line was obtained from Dr. Peter Chiang (Walter Reed Army Institute of Research) and cultured using Dulbecco's minimal essential medium (MEM: Grand Island Biological Co.) containing 10% fetal bovine serum. Cells were routinely started from frozen cultures every 6 weeks in order to assure that the cells used were from low passage cultures.

Uptake of Radioactive Thymidine and myo-Inositol

[methyl-$^3$H]Thymidine (New England Nuclear) incorporation was carried out using 96-well plates (Costar). Thymidine incorporation was used as an assay for cell viability, since in the previous studies described in the *Biochem. Biophys. Res. Commun.* (1983) article, other methods of assessing cell viability, including microscopic evaluation in the presence of trypan blue, gave identical results. Fifty $\mu$l of cell suspension ($4 \times 10^5$ cells/ml) were added to duplicate wells. Approximately 18 hours later 25 $\mu$l of the PI-containing liposomes were added to give a final concentration of phospholipid of 200 $\mu$M (approximately, 14 nmol/$2-3 \times 10^4$ cells). At various intervals after PI addition [$^3$H]thymidine, 1 $\mu$Ci/well was added and incubated with the cells for 3 hours. Cells were collected on glass fiber filter mats by a mechanical cell harvester (Skatron, Inc.) using a combination of scraping and fluid turbulence (saline). Filters were dried and the material was solubilized by incubation overnight with NCS tissue solubilizer and counted in the presence of Spectrafluor (Amersham).

[$^3$H]myo-Inositol incorporation was carried out as described for [$^3$H]thymidine incorporation except that after the cells were incubated with PI-containing liposomes the supernatant fluid was removed, [$^3$H]myoinositol, inositol, 1 $\mu$Ci/well, was added in inositol-free medium (special formulation, Grand Island Biological Co.) and the cells were incubated for 3 hours. The cells were harvested exactly as described for thymidine uptake.

When [$^3$H]myo-inositol PI was used [$^{14}$C]methyl thymidine (New England Nuclear) 0.1 $\mu$Ci/well was added to the cultures to assess cell viability. For inositol uptake studies [$^{14}$C]myo-inositol (Amersham Corp.) 0.1 $\mu$Ci/well was added in inositol-free medium. These changes were necessary due to the lower specific activities of the $^{14}$C-labeled radiochemicals.

Cell Culture Conditions for Studies on the Metabolic Fate of Phosphatidylinositol Cells were plated in 6-well plates (9.1 cm$^2$ Costar) using 3 ml of cell suspension/well ($2-3 \times 10^5$ cells/ml). The following day the supernatant fluid volume was reduced to 0.6 ml and 0.1 ml of liposome suspension was added (0.7 ml was sufficient to cover the cells) resulting in 150 nmol/$6-9 \times 10^5$ cells (the final concentration of PI was 200 $\mu$M). At the end of each incubation period the supernatant fluids were removed and the cells were carefully washed twice with PBS. The cells were then removed from the plates using a cell scraper (Costar) and suspended in two 0.5 ml rinsing aliquots of saline combined together. The cells were placed on ice before extraction.

Cell Extraction and Isolation of Radioactive Lipids

In order to extract lipids, methanol and chloroform were added to cell homogenates to obtain a single phase of CHCl$_3$:CH$_3$OH:H$_2$O (1:2:1 8, v/v) containing 0.1M HCl, according to Bligh and Dyer in *Can. J. Biochem. Physiology,* (1959) 37:911–937. Precipitated protein and cell debris were spun down at $1000 \times g$ for 5 minutes and the aliquots of the supernatant were used for the chromatographic analysis. The lipid compositions of the cell extracts were determined by thin layer chromatography on silica gel precoated sheets (E. M. Reagents; E. Merck, FRG) using the following solvent systems: (a) chloroform:methanol: acetic acid:water, 25:15:4:2 (v/v) (used for phospholipid separation): (b) 1-propanol:4.3M ammonia containing 10 mM EDTA, 65:35 (v/v) (used for PIP and PIP$_2$ separations); and (c) chloroform:acetone, 1:1 (v/v) (used for DG and fatty acid separations). All solvents used for thin layer chromatography were of highest purity.

Developed thin layer chromatography plates were cut in 1-cm segments which were placed in scintillation vials and assayed for radioactivity using Hydrofluor (National Diagnostics) scintillation fluid in a Mark III scintillation counter (Searle).

Protein Assay

Protein in cell homogenates was determined by a modified Lowry method in the presence of sodium dodecyl sulfate as described by Markwell et. al. *Anal. Biochem.* (1978) 87:206–210. Trypsinization of Cells After incubation with liposomes as described above, cells were washed twice with 1 ml of medium and further incubated with 0.025% trypsin in phosphatebuffered saline for 3 minutes at 37° C. The cells were not detached from the plates by this procedure. Trypsin was then removed, cells were harvested and lipids were extracted as above.

EXAMPLE I

Cytotoxic Effects of Synthetic Phosphatidylinositol

In order to utilize PI of precisely defined fatty acid composition, synthetic PI preparations each having a different substituted radioactive fatty acid in the sn-2 position were used. The rationale of this was based on the different fatty acid compositions that are known to exist between plant and animal PI. An example of a synthetic PI that mimics the fatty acid composition of plant PI is one that exclusively contains linoleic acid in the sn-2 position. Plant PI completely lacks arachidonic acid but the arachidonic acid content of animal PI is highly variable. Because of the possibility that arachidonic acid may influence cytotoxicity, synthetic PI containing exclusively either oleic or arachidonic acid in the sn-2 position was also utilized.

Figures 1A, 1B:
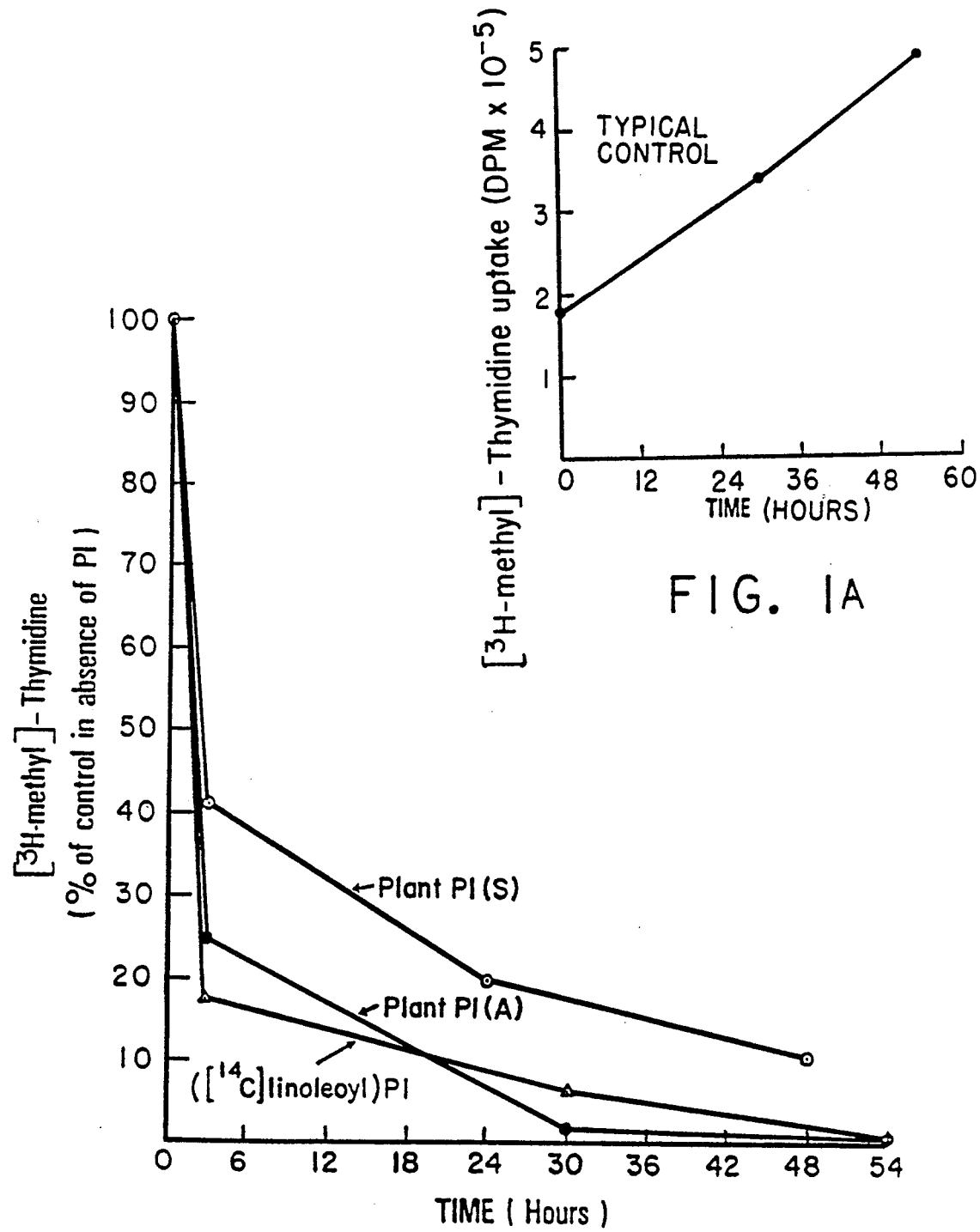
FIG. 1 shows the time course of thymidine uptake by N4TG1 neuroblastoma cells incubated with liposomes containing either synthetic or plant PI. Plant PI(S) is from the Sigma Chemical Company and plant PI(A) is from Avanti Polar Lipids, Inc. and ([$^{14}$C]linoleoyl)PI is the synthetic PI. The inset shows thymidine uptake of a typical control.
Figure 2A:
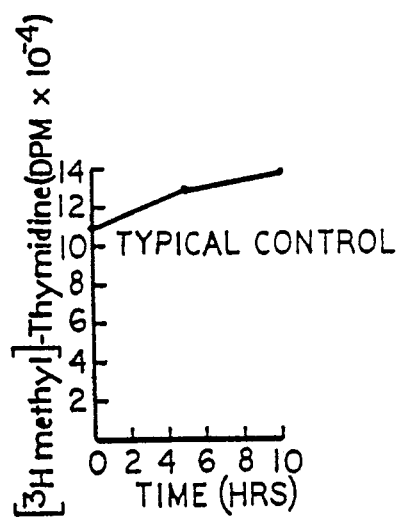
FIG. 2 shows the relationship between the sn2 fatty acyl composition of liposomal PI and the thymidine uptake pattern by N4TG1 neuroblastoma cells.
Figure 2B:
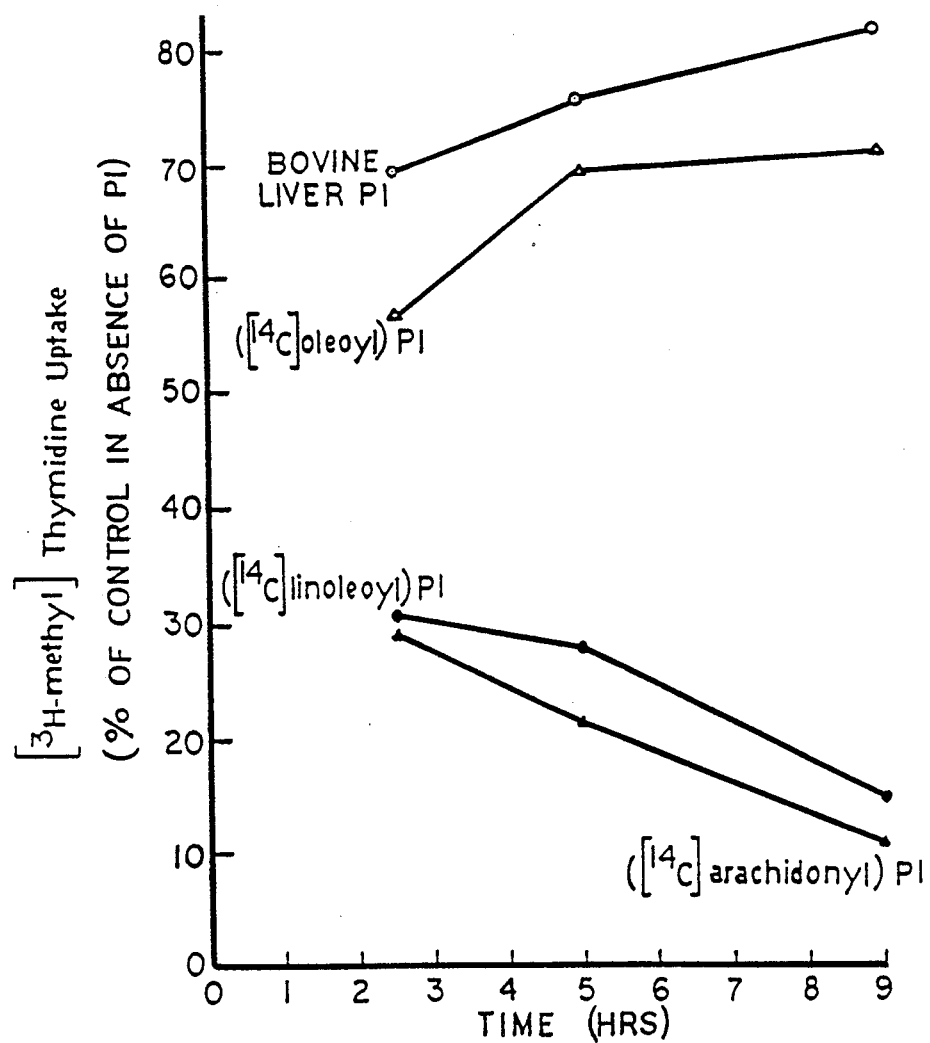

As shown in FIG. 1 ([$^{14}$C]linoleoyl)PI displayed cytotoxicity against N4TG1 neuroblastoma cells that was indistinguishable from that induced by plant PI. In contrast, ([$^{14}$C]oleoyl)PI was indistinguishable from animal (bovine liver) PI in that it lacked cytotoxicity (FIG. 2). Liposomes containing ([$^{14}$C]arachidonoyl)PI had considerable cytotoxicity against tumor cells and, therefore, had activity that was more similar to plant than to animal PI (FIG. 2).

In FIGS. 1 and 2 the curves were quite reproducible and representative experiments are shown. Because of fluctuations (<5%) in control values, the data were "normalized" by comparison with daily controls and expressed as "percentage of control in absence of PI."

Typical values for uptake of [$^3$H]thymidine by controls are shown in the inserts in FIGS. 1 and 2.

EXAMPLE II

Metabolic Fate of Exogenously Added PI

After incubation of liposomes containing PI with cells, one of two theoretical possibilities could occur: either the PI would or would not be metabolized by the cells. As shown in Table 1, significant uptake and metabolism of each of the above synthetic PI species occurred.

TABLE 1

FATE OF LIPOSOMAL PI AFTER INCUBATION WITH N4TG1 NEUROBLASTOMA CELLS
Control experiments revealed that in the absence of cells no degradation of PI; 100% of the radioactivity was identified as PI and quantitative recovery of PI was obtained.

| Liposomes Used | Incubation Time (H) | [$^{14}$C]Labeled Lipids Bound (nmol/mg Protein) | Fatty Acids | DG | Fatty Acid:DG | Phosphatidylcholine | PI |
|---|---|---|---|---|---|---|---|
| [$^{14}$C]Linoleoyl)PI | 3 | 193 (100)[a] | 4.3 | 0.8 | 5.4 | 4.4 | 90.5 |
|  | 11 | 317 (100) | 1.3 | 0.8 | 1.4 | 3.2 | 94.6 |
| [$^{14}$C]Oleoyl)PI | 3 | 20 (100) | 6.0 | 3.5 | 1.7 | 3.4 | 87.1 |
|  | 11 | 148 (100) | 2.0 | 2.5 | 0.8 | 1.9 | 93.6 |
| [$^{14}$C]Arachidonoyl)PI | 3 | 74 (100) | 3.9 | 2.2 | 1.8 | Not Detected | 93.9 |
|  | 11 | 200 (100) | 1.9 | 3.0 | 0.6 | Not Detected | 95.1 |
| [$^3$H]myo-Inositol)PI (diluted in bovine liver PI) | 3 | 20 (100) |  |  |  |  | 100 |
|  | 11 | 61 (100) |  |  |  |  | 100 |

[a]Numbers in parentheses show recovery percentage.

The degree of uptake of PI was dependent on the nature of the fatty acid in the sn-2 position, namely, linoleoyl- ≥ arachidonoyl > oleoyl > bovine liver PI. Prolonged incubation (11 hours) considerably increased the amount of radioactive PI taken up by the cells. The differential uptake of liposomal PI shown in Table 1 differs from the previous observation of lipsomal cholesteryl oleate reported in *Biochem. Biophys. Res. Comm.* (1983) article. These differences may have been related to the ability of PI to exchange with or transfer to cell membrane lipids.

After incubation of cells with PI liposomes, analysis of radioactive lipids extracted from the cells clearly showed the presence of radioactive-free fatty acids. The percentage of radioactivity taken up by the cells that appeared as radioactive-free fatty acids was approximately the same with each liposomal PI used. However, the percentage of radioactive-free fatty acids that appeared decreased between 3 and 11 hours.

Metabolism of PI might be expected to yield DG in addition to free fatty acids. As shown in Table 1 radioactive DG did appear in significant quantities at both 3 and 11 hours and the relative percentage of radioactivity did not change significantly with time. Because of the decrease of free fatty acids with time and the lack of such changes in DG, the fatty acid DG ratio decreased with time.

Further metabolism of PI might be expected to result in the appearance of other radioactive phospholipid species. Upon using the solvent system designated to separate phospholipids by thin layer chromatography, the only phospholipid detected was PC and it was found with ([$^{14}$C]linoleoyl)PI and with ([$^{14}$C]oleoyl)PI but not with ([$^{14}$C]arachidonoyl)PI (Table 1). In each case most of the recovered radioa activity remained as intact PI which had the identical chromatographic properties as liposomal PI initially presented to the cells.

Particular care was taken to examine whether PIP and PIP$_2$ became labeled after incubating cells with ([$^3$H]myo-inositol PI. Careful analysis including special solvent systems that would optimize separation of radioactive PIP and PIP$_2$ failed to reveal the appearance of these compounds under the experimental conditions described. In the above analysis, all of the recovered $^3$H that was detected was identified as being present with PI.

Treatment of cells with trypsin did not reveal the cellular site of metabolism of lipsomal PI, although it did suggest that 95% of the liposomes were surface associated. Regardless of whether the liposomal PI was sensitive or resistant (5-6% of the radioactivity was resistant) to removal from the cells by trypsin, similar types of radioactive degradation products were detected in the extracted cellular lipids.

EXAMPLE III

Effect on Cells of lyso-PI and Linoleic Acid Presented Extracellularly

The observation that there was intracellular generation of free fatty acids and the concomitantly produced lyso-PI suggested that these toxic products may have contributed to the cytotoxicity observed. These compounds were each tested separately in order to see if toxicity could be observed at the levels generated intracellularly. Liposomes containing lyso-PI: cholesterol, 2:1, were added to cell cultures as described in the above "Materials and Methods" section. In parallel cultures liposomes containing as the phospholipid either plant, yeast, or animal PI together with cholesterol were used. FIG. 9 shows that liposomes containing lyso- or plant PI showed similar patterns of depresed thymidine uptake while the yeast and animal PI preparations did not affect thymidine uptake.

Since free fatty acids have been observed to be toxic to cultured cells when added extracellularly, linoleic acid was presented in liposomes made up of nontoxic PI preparations (yeast or animal PI) and cholesterol. Table 2 shows that decreased thymidine uptake occurred with both liposomal preparations. Cellular uptake of linoleic acid was calculated based on uptake of tracer $^3$H-linoleic acid. In Table 1 intracellularly generated free fatty acids occurred at a concentration of 2.2 nmol/8×10$^5$ cells. In Table 2, when liposomes contained animal PI as the phospholipid, the intracellular uptake was 2.55 nmol/8×10$^5$ cells and a 63% decrease in thymidine incorporation compared with controls was observed. In the case of liposomes containing yeast PI as the phospholipid, the uptake of linoleic acid was 2.9 nmol/8×10$^5$ cells and the thymidine incorporation had decreased to 53% of control values. Although toxicity occurred at similar concentrations of fatty acids as were generated intracellularly it must be kept in mind that in the experiment in Table 2 there were also extracellular free fatty acids which could exert effects on the outer surface of the cells.

EXAMPLE IV

Liposomes Containing Mixtures of Two PI Species

Figure 3A:
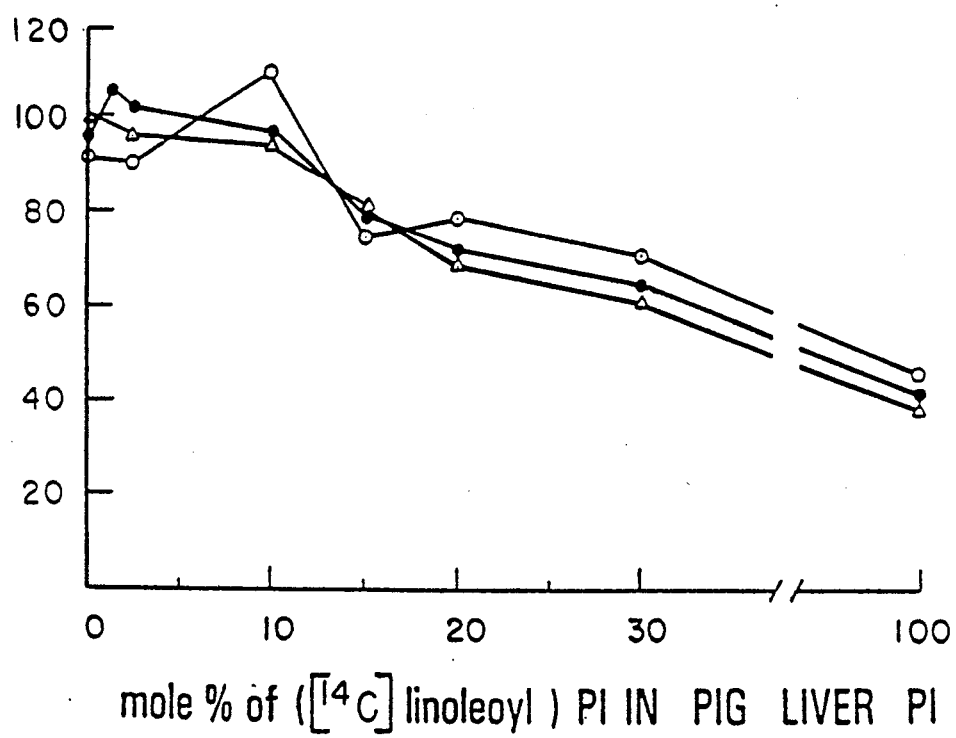
FIGS. 3a and 3b show the effect of increasing the molar fraction of synthetic PI or animal PI in liposomes on (a) thymidine uptake (FIG. 3a) and myo-inositol uptake (FIG. 3b) by N4TG1 neuroblastoma cells, ⊙ 100 μm PI, ● 200 μm PI, ▲ 300 μm PI. Cells were incubated with liposomes made up of the various combinations indicated (mol %) of ([$^{14}$C]linoleoyl)PI and animal PI.
Figure 3B:
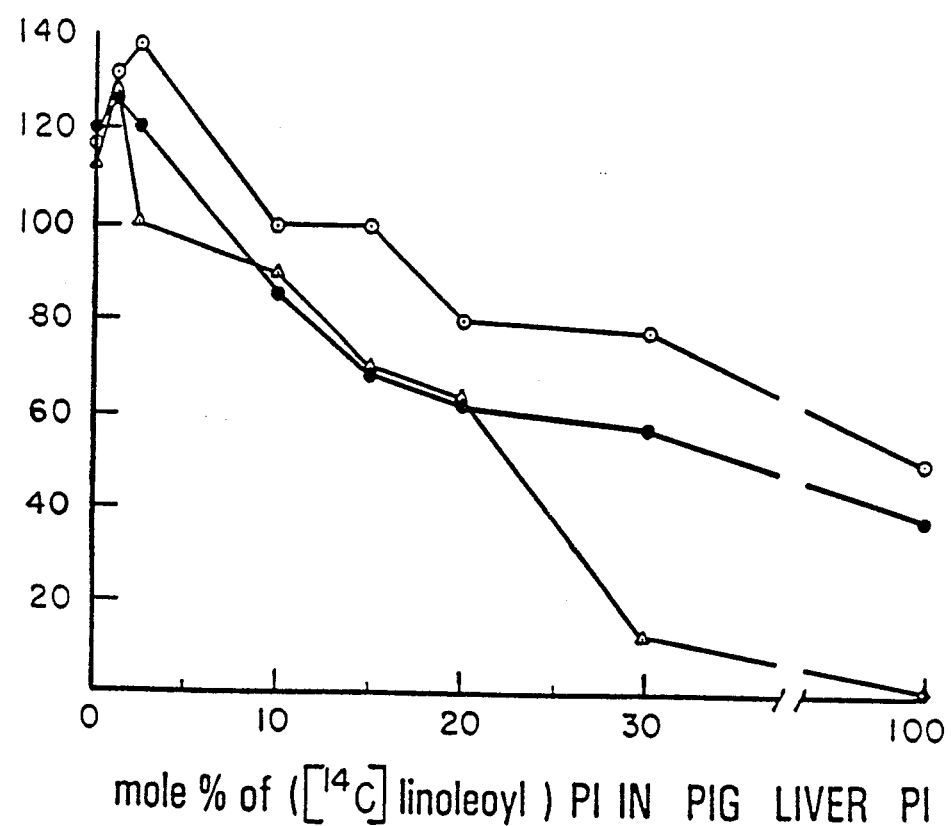

In all of the above experiments liposomes contained PI that was derived from only one source. The question, therefore, arose as to whether mixtures of cytotoxic and non-cytotoxic PI would retain cytotoxicity and if so to what degree. A gradually increasing mole fraction of cytotoxic PI, ([$^{14}$C]linoleoyl)PI, was combined with a gradually decreasing mole fraction of a non-cytotoxic animal PI (porcine liver) containing 1% arachidonic acid. Regardless of whether cytotoxic PI was completely substituted for non-cytotoxic PI or added only in gradually increasing amounts, cytotoxicity as determined by uptake of [$^3$H]thymidine (FIG. 3a) or [$^3$H]myo-inositol (FIG. 3b) was still manifested.

TABLE 2

EFFECT ON CELLS BY LINOLEIC ACID IN LIPOSOMES MADE OF NON-CYTOTOXIC PHOSPHOLIPIDS

| Phospholipid | Thymidine Uptake in the Presence of Various Concentrations of Linoleic Acid | | |
|---|---|---|---|
| | 50 μM | 100 μM | 200 μM |
| Animal Phosphatidylinositol | 63 (2.55)$^a$ | 44.5 (3.03) | 27.4 (10.4) |
| Yeast Phosphatidylinositol | 80 (1.8) | 53 (2.9) | 23.2 (14.8) |

$^a$Numbers in parentheses, uptake of linoleic acid in nmol/8 × 10$^5$ cells.

RESULTS

One difference between the results reported in the article (*Biochem. Biophys. Res. Commun.* (1984) 114:863–871) and this invention is the fact that in the article, [$^{14}$C]cholesteryl oleate was included as a trace marker to determine the fate of the drug. As a consequence of its inclusion, the cholesteryl oleate became an integral part of the drug since the phosphatidylinositol, cholesterol, and cholesteryl oleate were dried together from the organic solvent and resuspended in saline. Prior to this invention, applicants had no other way to determine the fate of the liposomes. Now, it has been found that the use of drug containing cholesterol and a synthetic phospholipid containing a [$^{14}$C]radioactive label enables one to achieve unexpectedly superior results (Table 3) which were not apparent or obvious based on the results of prior research conducted in this field. This synthetic preparation of ([$^{14}$C]linoleoyl)PI showed the same pattern of toxicity to tumor cells as did plant PI as shown in FIG. 1. The prevous article in *Biochem. Biophys. Res. Commun.* implied that cholesteryl oleate was a necessary part of the preparation of cytotoxic effects. The present invention involves a preparation which does not utilize cholesteryl oleate. The only necessary component is a phospholipid having appropriately unsaturated fatty acids in the sn-2 position.

It has been discovered that cholesteryl oleate dramatically alters the toxicity of the drug by causing larger (more readily sedimentable) liposomes to be formed.

TABLE 3

LD$_{50}$ TO TUMOR CELLS OF VARIOUS PREPARATIONS OF PI

LD$_{50}$ values are reported in μM concentrations; N.D. = not determined; values which are <25 μM are the result of 100% kill at 50 μM, the lowest dose used in these studies.

| Cell Lines | ([$^{14}$C]linoleoyl)PI | | Avanti PI | Plant PI/Chol./Ol. (B B R C Article) |
|---|---|---|---|---|
| | 3 hours | 8 hours | 3 hours | 48 hours |
| WI-38/SV-40 | 65 | 35 | N.D. | 135 |
| N4TG1 Neuroblastoma | 25 | 25 | 25 | 70 |
| SK-N-MC | 39 | 38 | N.D. | 180 |
| HT-144 | 25 | 25 | N.D. | 205 |
| Ehrlich Ascites | N.D. | N.D. | 65 | 125 |

Figure 4A:
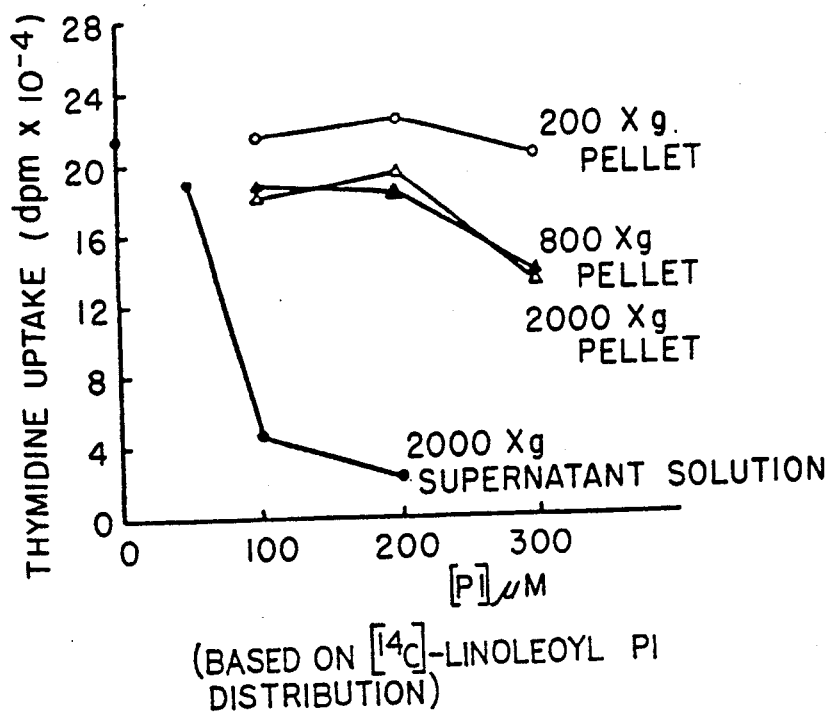
FIGS. 4a and 4b depict the cytotoxicity to tumor cells induced by various fractions of plant PI/cholesterol (2:1) liposomes containing trace amounts of either ([$^{14}$C]linoleoyl)PI (FIG. 4a) or ([$^{14}$C]cholesteryl) oleate (FIG. 4b). In both FIGS. 4a and 4b, pellets 1, 2, and 3 were obtained by differential centrifugation. Very small liposomes did not pellet by the g forces used but remained in the supernatant solutions.
Figure 4B:
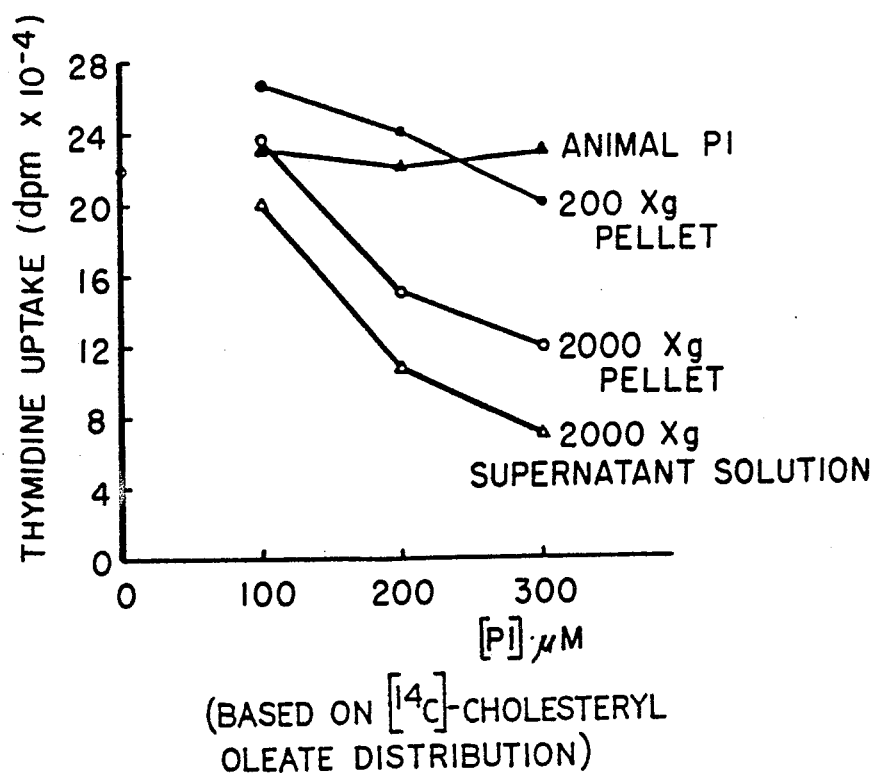

Only 8% of the liposome drug (using the "self" marker of synthetic ([$^{14}$C]linoleoyl)PI) were sedimented by low speed centrifugation, whereas 67% of the liposomes sedimented under the same conditions when [$^{14}$C]cholesteryl oleate was used as the marker for liposomes. This represents an increase of nearly 800%. Based on the experimental results, it has been have found that cholesteryl oleate had altered the size of the liposome drug which was formed. Additionally, using ([$^{14}$C]linoleoyl)PI, it was observed that the liposome drug which did not sediment (92% of the preparation), is comprised of small liposome vesicles, was far more effective on a molar basis than the pelleted liposomes, as illustrated in FIG. 4a. In contrast, for the preparation which contained cholesteryl oleate, only 33% of the lipsomes were not sedimented, again the non-sedimentable vesicles were more effective in killing tumor cells than the larger, sedimentable liposomes in the same preparation, as shown in FIG. 4b.

This demonstrates that small size, nonsedimentable liposomes were clearly a more effective drug preparation than the larger, sedimentable liposomes in terms of their potency for killing tumor cells.

Synthetic ([$^{14}$C]linoleoyl)PI functions substantially identically in terms of toxicity to plant PI obtained from Avanti Polar Lipids, Inc. (Birmingham, AL), and both were slightly more effective as compared to the plant PI obtained from Sigma Chemical Co. (St. Louis, MO). Toxicity data are presented in FIG. 1. Our current data indicates that the fatty acid composition in the sn-2 position of the phospholipid is the factor which influences the toxicity. Fatty acid (FA) composition in the sn-2 position of the three PI preparations are as shown in Table 4.

TABLE 4

FATTY ACID COMPOSITION OF PHOSPHATIDYLINOSITOL PREPARATIONS

|  | Linoleic acid in sn-2 position | % Unsat. FA in sn-2 position | % PI |
|---|---|---|---|
| ([$^{14}$C]linoleoyl)PI | 100% | 100% | 100% |
| Avanti PI (Plant) | 97% | 100% | 100% |
| Sigma PI (Plant) | 84% | 94% | 97% |

This tabular data confirms that ([$^{14}$C]linoleoyl)PI is virtually chemically identical to the commercial preparation of plant PI obtained from Avanti Polar Lipids, Inc., and is very similar to that obtained from Sigma Chemical Co. The slight decrease in toxicity caused by Sigma Plant PI may relate to the fact that it is slightly contaminated with nontoxic phosphatidylcholine (3%) and also the fatty acid composition in the sn-2 position is not as unsaturated as for the other two preparations.

In Table 3 the drug dose which resulted in a 50% kill of tumor cells was determined by the same method described on page 867 of the *Biochem. Biophys. Res Commun.* article cited above. The LD$_{50}$ values for some of the cell lines reported in the *Biochem. Biophys. Res. Commun.* article are compared with LD$_{50}$ values obtained using Avanti plant PI or synthetic ([$_{14}$C]linoleoyl)PI.

Applicants novel compositions, which lack cholesteryl oleate (column 1, Table 3) are 2–10 fold more effective than those reported in the *Biochem. Biophys. Res Commun.* article (column 3, Table 3) which required the presence of the cholesteryl oleate. Additionally, the time required for the increased effectiveness of the instant compositions is decreased by sixteen (16) fold.

The graphs in FIGS. 5–7a show that PI and PC with the same fatty acid in the sn-2 position display similar patterns of cytotoxicity in a variety of cell lines. Only three tumors and one normal line are reported for the sake of simplicity. The response of cells to the cytotoxic phospholipids seems to be represented by a spectrum of which normal cells are simply at the end of the spectrum showing relatively little cytotoxicity. In contrast, neuroblastoma cells (N4GT1), glioblastoma cells (SK-N-MC), and virally infected cells (WI-38/SV-40) are quite easily killed by these phospholipids which contain either linoleic acid (FIGS. 5 and 5a) or arachidonic acid (FIGS. 6 and 6a) in the sn-2 position. As shown in FIGS. 7 and 7a, with oleic acid in the sn-2 position, little effect on any of the tumor or normal cells is observed.

The data in Table 5 was obtained concomitantly with the toxicity studies in FIGS. 5–7a. This table shows the uptake of various preparations of PI or PC by normal and transformed (tumor) cells. More specifically, uptake of the phospholipids shows that for normal cells, MRC-5, (column 1) there is a similar low uptake of all of the phospholipids. The lowest uptake is with the nontoxic preparation of naturally occurring animal PI. (Previous studies [*Cancer Res.* Oct. 1, 1985] show that synthetic ([$^{14}$C]linoleoyol)PI shows virtually identical toxicity to that observed with naturally occurring plant PI).

The toxic phospholipid preparations were taken up proportionately to the degree of toxicity observed. In general, the highest uptake was seen with the mouse neuroblastoma cell line, N4TG1. HT-144, a human melanoma cell line, also showed high levels of lipsomal uptake which correlated with high toxicity. The W1-38/SV-40 transformed cells show lesser degrees of toxicity and uptake than some of the other cell lines. The data differed from previous observations in which [$^{14}$C]cholesteryl oleate was used as the marker of liposome uptake.

The data regarding the varying degrees of uptake and its correlation with toxicity, as shown in FIGS. 5–7a and Table 5, suggest a clear relationship between the two parameters. Furthermore, other data (Table 1) show that uptake correlates with the production of free fatty acids, shown to be toxic to the cells (*Cancer Res.*, Oct. 1, 1985).

TABLE 5

LIPOSOMAL UPTAKE BY NORMAL AND TUMOR CELLS
(nMoles of phospholipid/1 × 10$^5$ cells)

|  | Normal Cells | Tumor Cells | | | |
|---|---|---|---|---|---|
|  | MRC-5 | WI-38/SV-40 | N4TG1 | SK-N-MC | HT-144 |
| ([$^{14}$C]oleoyl)PI | 0.13 | 0.21 | 0.28 | 0.28 | 0.28 |
| ([$^{14}$C]oleoyl)PC | 0.09 | — | 0.26 | 0.26 | 0.28 |
| ([$^{14}$C]linoleoyl)PI | 0.09 | 0.39 | 0.39 | 0.45 | 0.39 |
| ([$^{14}$C]linoleoyl)PC | 0.09 | 0.32 | 0.45 | 0.45 | 0.45 |
| ([$^{14}$C]arachidonoyl)PI | 0.09 | 0.33 | 0.49 | 0.39 | 0.55 |
| ([$^{14}$C]arachidonoyl)PC | 0.08 | — | 0.73 | 0.40 | 0.66 |

TABLE 5-continued
LIPOSOMAL UPTAKE BY NORMAL AND TUMOR CELLS
(nMoles of phospholipid/1 × 10⁵ cells)

| | Normal Cells | | Tumor Cells | | |
|---|---|---|---|---|---|
| | MRC-5 | WI-38/SV-40 | N4TG1 | SK-N-MC | HT-144 |
| Pig Liver PI ([2-³H]myo-inositol) | 0.08 | 0.19 | 0.22 | 0.15 | 0.13 |

These facts, taken together, implicate the action of phospholipase $A_2$, the enzyme responsible for releasing free fatty acids from the sn-2 position of phospholipids, and concomitantly producing a second toxic product lyso-PI. Phospholipase $A_2$ is known to be most active against phospholipids containing unsaturated fatty acids in their sn-2 position, such as linoleic (18:2) or arachidonic (20:4) acids, rather than less unsaturated fatty acids such as oleic acid (18:1) or palmitic acid (16:0). Free fatty acids themselves are also toxic to tumor cells (Table 2). Lyso-PI is also toxic to the tumor cells (FIG. 8). It is likely that in the present invention some of the toxicity to tumor cells is due to the production of free fatty acids and lyso-PI released by phospholipase $A_2$.

In order to test this hypothesis, use of quinacrine, an inhibitor of phosphalipase $A_2$ was tried. Quinacrine itself is somewhat cytotoxic to tumor or normal cells (FIG. 9a). When quinacrine was used in conjunction With plant PI a reversal of cytotoxicity was seen (FIG. 9b). Due to the non-specific toxicity of quinacrine, caution must be used in interpreting the inhibition studies. However, it definitely appears that there is competition between quinacrine and plant PI.

Several specific inhibitors were used with lung small cell carcinoma cultures. These cells grow in relatively large non-dissociable clusters and show $LD_{50}$ of 72 $\mu$M, based on thymidine uptake. In humans, this type of lung cancer is fatal very soon after detection. In FIGS. 9c and 9d, quinacrine, the inhibitor of phospholipase $A_2$, is shown to be extremely toxic itself to these cells, as is plant PI. No competition was observed in this case (very likely because both compounds are so highly toxic to these cells.)

Two inhibitors of prostaglandin synthesis were used, indomethecin and eicosanotetraynoic acid, a structural analog of arachidonic acid. These inhibitors showed relatively little promise of blocking the toxicity of plant PI (FIGS. 9c and d). In Table 6, the production of prostaglandin $E_2$ by normal, transformed and tumor cells in the presence and absence of plant PI is shown. By direct measurement, prostaglandin $E_2$ production is markedly decreased in tumor cells by treatment with plant PI. That may be a result of cell death rather than a cause of it. In contrast, normal cells (MRC-5 and WI-38) seem to be stimulated to produce prostaglandin $E_2$ by treatment with plant PI (Table 6).

The experimental work performed with pleiotropic drug resistant cells show that plant PI is very effective in treating cells which have developed a resistance to general metabolic inhibitors (FIG. 10). The $LD_{50}$ of these cells is approximately 25 $\mu$M. This is among the lowest $LD_{50}$ detected for any cell type.

To further demonstrate the subject invention multi-drug resistant cells were tested. MCF-7 cells were continuously exposed to increasing concentrations of adriamycin resulting in multidrug-resistance (mdr) as a stable genetic trait (Batist et al., J. Biol. Chem. (1986) 261:155,544–155,549). The mdr cells are referred to as $ADR^R$ cells. MCF-7 WT (wild-type) and $ADR^R$ cells were plated at 1000 cells/well (9.6 cm²) in RPMI 1640 supplemented with 10% fetal bovine serum (day 1). Plant PI (0.5–150 $\mu$M) in the form of multilamellar vesicles (Jett and Alving, in Methods in Enzymology 141B (eds. Conn. P.M. and Means A.R.) 459–466, Academic Press, Orlando, FL 1987) or adriamycin (1–2000 nM) was added to the cultures on day 2. At day 8–10, the fluid was removed and clones were fixed, stained and counted. Colonies were scored positive if >40 cells/clone Adriamycin (10–500 nM) or plant PI (20–200 $\mu$M) was added at the time of cell plating. At day 8–10, the colony forming units of granulocytes and monocytes (CFV-GM) were counted. The results were the average of triplicate experiments. The $IC_{50}$ values for adriamycin was 80 nM, while for plant PI it was 50 nM. Human marrow CFV-GM were found to be less sensitive to plant PI than either WT or $ADR^R$ cells.

In order to further assess cell viability between wild-type (MCF-7 wild-type cell line) (WT) and multi-drug resistant MCF-7 $ADR^R$ ($MDR^R$) breast cancer cells, tests involving TCA-precipitable 2-[³H]methylthymidine incorporation were employed. MCF-7 WT and $ADR^R$ cells were plated (Day 1) at 1500 cells/well in 96-well cluster plates. On Day 2, phospholipid preparations were added to triplicate cultures. On Day 7, 2-[³H]methylthymidine was added and the cells harvested as described (Jett et al., Cancer Res. (1985) 45:4810–4815), using 5% TCA as the wash buffer. Results were expressed as the geometric mean of triplicate cultures. A 7.4-fold difference in the $IC_{50}$ for $ADR^R$ and WT cells was observed, being 4.5 and 33 $\mu$M, respectively. Examination of toxicity induced by other phospholipids showed a predictable pattern of toxicity, with yeast PI (containing primarily saturated fatty acids) and synthetic distearoyl phosphatidyl choline showing no toxicity to either cell line. Synthetic phosphatidyl choline containing linoleic acid in the sn-2 position was found to be not as toxic as synthetic phosphatidylinositol containing the identical fatty acids (Jett et al. (1985), supra), nor was it as toxic as the naturally occuring plant PI.

SUMMARY OF THE RESULTS

Our original observation showed that PI of plant origin, but not of animal origin, was toxic to tumor cells but not to normal cells (Biochem. Biophys. Res. Commun. (1983) 114:863). Other phospholipids tested were found to be non-toxic.

The selective cytotoxicity to tumor cells initially appeared to be unique to liposomes containing plant PI and cholesteryl oleate. Our present data, using liposomes that lack cholesteryl oleate, show that certain synthetic phospholipids produce the same effect. Specifically, synthetic PI or synthetic phosphatidylcholine (PC) preparations containing highly unsaturated fatty acids in the sn-2 position are toxic to tumor cells but not to normal cells. In contrast, synthetic PI or PC preparations with oleic acid in the sn-2 position, or animal PI, substituted with [³H]-myoinositol, do not show toxicity to tumor or normal cells. Plant PI contains linoleic acid as the sn-2 fatty acid, while animal PI is immensely more diverse and depends on the animal and organ source of the PI.

Phospholipase $A_2$ inhibitors have been examined to see if they blocked the toxicity of plant PI. Phospholipase $A_2$ inhibitors, themselves, depress thymidine uptake and many cell functions. Despite that observation, it is clear that the phospholipids compete with the inhibitor for the enzyme.

Ninety-one percent of the metabolic products generated intracellularly from liposomally supplied PI, are products of the enzymatic activity of phospholipase $A_2$ (free fatty acids, PC, and the concomitantly produced lyso-PI). The remaining product is diglycerides. Moreover, one striking observation in these experiments is that the toxic PI preparations are taken up to a far greater extent than nontoxic PI preparations. Normal cells take up the same low amounts of toxic and nontoxic phospholipids.

It is evident from the above results, that the phosphatides having a polyunsaturated carboxylic acid at the 2 position are effective agents in inhibiting tumor growth. The subject compositions are operative over a wide variety of tumors, while being substantially benign toward normal cells. In this manner, the subject compositions provide for substantial selective advantage between tumor cells and normal cells. In addition, the subject compositions may be used with other cytotoxic agents at substantially reduced levels, where the combination may provide for substantially higher cytotoxic effect. Furthermore, data show that the subject compositions are particularly effective with cells which are shown to be multiple-drug resistant. In this way, the subject compositions have an added advantage, where the effectiveness of the subject compositions is enhanced where the tumor cells may demonstrate an enhanced resistance to other cytotoxic drugs.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

What is claimed is:

1. A method for inhibiting the proliferation of rapidly proliferating abnormal mammalian cells, said method comprising:
contacting said cells with a cell proliferating inhibiting amount of a diacyl phosphatide, wherein the sn2-acyl group is a polyunsaturated fatty acid, said contacting being in the substantial absence of non-phosphatidic fatty acid esters having fewer than 2 olefinic sites of unsaturation in the fatty acid of said ester, for a sufficient time to inhibit said proliferation.

2. A method according to claim 1, wherein said phosphatide is contacted in the form of a liposome.

3. A method according to claim 2, wherein said liposome comprises cholesterol.

4. A method according to claim 1, wherein said sn2-acyl group is linoleoyl.

5. A method according to claim 4, wherein said diacyl is dilinoleoyl.

6. A method according to claim 1, wherein said sn2-acyl group is arachidonyl.

7. A method according to claim 1, wherein said cells are tumor cells.

8. A method according to claim 7, wherein said tumor cells are of the mdr phenotype.

9. A method for inhibiting the proliferation of neoplastic mammalian cells, said method comprising:
contacting said cells with a cell proliferating inhibiting amount of a plant diacyl phosphatide composition, wherein the sn2-acyl group is a polyunsaturated fatty acid, said contacting being in the substantial absence of non-phosphatidic fatty acid esters having fewer than 2 olefinic sites of unsaturation in the fatty acid of said ester, for a sufficient time to inhibit said proliferation.

10. A method according to claim 9, wherein said plant composition is a purified soybean composition.

11. A liposome composition consisting essentially of a purified plant phosphatide composition and optionally cholesterol in a tumor cell inhibiting amount in a pharmacologically acceptable carrier.

12. A liposome composition consisting essentially of a synthetic phosphatide having a polyunsaturated fatty acid at the sn2-position and optionally cholesterol in a tumor cell inhibiting amount in a pharmacologically acceptable carrier.

13. A liposome composition according to claim 12, wherein said phosphatide is an inositide.

14. A liposome composition according to claim 12, wherein said phosphatide is a choline.

15. The method of claim 1 wherein the lipid consist essentially of a phosphatide having the formula $$\begin{array}{c} \text{CH}_2\text{—O—}\overset{\overset{\displaystyle O}{\|}}{\text{C}}\text{—R}_1 \\ | \\ \text{CH—O—}\overset{\overset{\displaystyle O}{\|}}{\text{C}}\text{—R}_2 \\ | \\ \text{CH}_2\text{—O—}\overset{\overset{\displaystyle O}{\|}}{\text{P}}\text{—R}_3 \\ | \\ \text{O}^{\ominus} \end{array}$$

wherein $R_1$ and $R_2$ are aliphatic hydrocarbons and $R_3$ is a

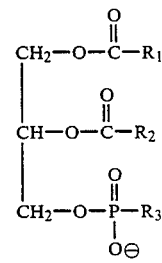—OH (inositol), $-CH_2-CH_2-\overset{\oplus}{N}(CH_3)_3$ (choline),

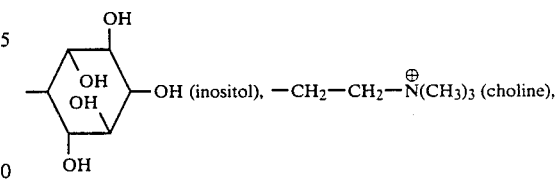

$-O-CH_2-CH_2 \overset{\oplus}{N}H_3$ (ethanolamine), or $-O-CH_2-CHOH-CH_2OH$ (glycerol).

16. The method of claim 15 wherein cholesterol is present with the phosphatide.

17. A method of claim 15 wherein the lipids present in the lipid mixture are a phosphatide and free fatty acid.

18. The method of claim 15 wherein $R_2$ is a fatty acid having unsaturated bonds.

19. The method of claim 18 wherein $R_2$ is $-(CH_2)_7-CH=CHCH_2CH=CH(CH_2)_4CH_3$.

20. The method of claim 18 wherein $R_2$ is $-CH_2CH_2(CH_2CH=CH)_4(CH_2)_4CH_3$.

21. The method of claim 1 wherein said cells are selected from the group comprising mammary carcinoma, lymphoid, neuroblastoma, glioblastoma, small cell lung carcinoma, lung carcinoma, melanoma, ascites, ovarian carcinoma, and bladder carcinoma.

22. The method of claim 8 wherein the tumor cell infection is a mammary carcinoma.

23. The method of claim 9 wherein the type of mammary carcinoma is MCF-7-KC control or MCF-7-KC-ADR drug resistant cells.

24. The method of claim 21 wherein the tumor cell infection is of lymphoid origin.

25. The method of claim 24 wherein the type of lymphoid cell infection is selected from the group comprising promeylocytic leukemia (HL-60) and Raji (burkitt lymphoma).

26. The method of claim 21 wherein the tumor cell infection is a neuroblastoma.

27. The method of claim 26 wherein the type of neuroblastoma is human neuroblastoma (SK-N-MC).

28. The method of claim 27 wherein the tumor cell infection is a glioblastoma.

29. The method of claim 28 wherein the type of glioblastoma is U87MG.

30. The method of claim 21 wherein the tumor cell infection is a small cell lung carcinoma.

31. The method of claim 30 wherein the type of small cell lung carcinoma is NCI-H49.

32. The method of claim 30 wherein the type of small cell lung carcinoma is NCI-H128.

33. The method of claim 21 wherein the tumor cell infection is a lung carcinoma.

34. The method of claim 33 wherein the type of lung carcinoma is SK-MES-1.

35. The method of claim 21 wherein the tumor cell infection is a melanoma.

36. The method of claim 35 wherein the type of melanoma is HT-144.

37. The method of claim 21 wherein the tumor cell infection is an ascites.

38. The method of claim 37 wherein the type of ascities is Strain E (Ehrlich-Lettre Ascites carcinoma).

39. The method of claim 21 wherein the tumor cell infection is an ovarian carcinoma.

40. The method of claim 38 wherein the type of ovarian carcinoma is OVCAR 3.

41. The method of claim 1 wherein the treatment to the cell is effected prior to transplantation of the cells from one growth site to another.

42. The method of claim 1 wherein the treatment is effected subsequent to tumor cell growth.

43. The composition according to claim 12 wherein the phosphatide is represented by formula

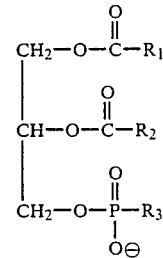

wherein $R_1$ and $R_2$ are aliphatic hydrocarbons and $R_3$ is a

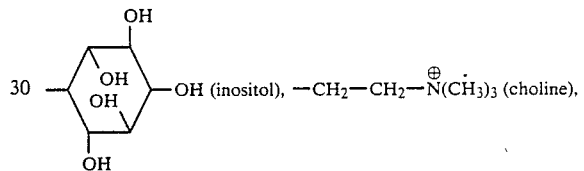

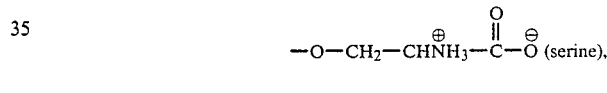

$-O-CH_2-CH_2 \oplus NH_3$ (ethanolamine), or $-O-CH_2-CHOH-CH_2OH$ (glycerol).

44. The composition of claim 43 wherein cholesterol is present in a ratio with the phosphatide.

45. The composition of claim 43 wherein the lipids present in the lipid mixture are a phosphatide and free fatty acid.

46. The composition of claim 43 wherein $R_2$ is a fatty acid having unsaturated bonds.

47. The composition of claim 46 wherein $R_2$ is $-(CH_2)_7CH=CHCH_2CH=CH(CH_2)_4CH_3$.

48. The composition of claim 46 wherein $R_2$ is $CH_2CH_2(CH_2CH=CH)_4(CH_2)_4CH_3$.

* * * * *